US012743457B2

(12) United States Patent
Das

(10) Patent No.: US 12,743,457 B2
(45) Date of Patent: Sep. 22, 2026

(54) METHOD AND SYSTEM FOR GENERATING SEMANTIC RESPONSE TO QUERY

(71) Applicant: NEC Corporation, Tokyo (JP)

(72) Inventor: Avijit Das, Bangalore (IN)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 19/090,509

(22) Filed: Mar. 26, 2025

(65) Prior Publication Data

US 2025/0307296 A1 Oct. 2, 2025

(30) Foreign Application Priority Data

Mar. 30, 2024 (IN) ............................ 202441026523

(51) Int. Cl.
*G06F 16/338* (2019.01)
*G06F 16/35* (2025.01)
*G16H 10/60* (2018.01)

(52) U.S. Cl.
CPC ............ *G06F 16/338* (2019.01); *G06F 16/35* (2019.01); *G16H 10/60* (2018.01)

(58) Field of Classification Search
CPC ........ G06F 16/338; G06F 16/35; G16H 10/60
See application file for complete search history.

(56) References Cited

U.S. PATENT DOCUMENTS 8,751,495 B2 * 6/2014 Chung .................. G16H 50/70 707/802
10,943,673 B2 * 3/2021 Zhang ................ G06F 40/137
2014/0108423 A1 * 4/2014 Casella dos Santos .................... G06F 16/285 707/769
2016/0019299 A1 * 1/2016 Boloor ................. G06F 16/367 705/3
2018/0173850 A1 * 6/2018 Heinrich ............... G16H 10/60
2020/0327964 A1 * 10/2020 Zhang .................. G06F 40/295
2021/0027894 A1 * 1/2021 Rich ...................... G16H 10/60
2021/0225466 A1 * 7/2021 Barkan .................. G06F 16/35
2023/0360752 A1 * 11/2023 Ozeran .................. G06Q 10/06
2024/0054280 A1 * 2/2024 Bourez ................. G06F 40/103
2024/0111999 A1 * 4/2024 Laish ..................... G06N 3/048
2025/0252952 A1 * 8/2025 Khair ...................... G10L 15/16

* cited by examiner

*Primary Examiner* — Jared M Bibbee
(74) *Attorney, Agent, or Firm* — Sughrue Mion, PLLC

(57) ABSTRACT

The implementations of the present disclosure provide a method and a system for generating a semantic response to a query. The method comprises receiving unstructured continuous data of a user, classifying the unstructured continuous data into a first type of data, by a first classification model, a second type of data, by a second classification model, and a third type of data, by a third classification model, wherein the second and third type of data includes name related data and event related data respectively. The method further comprises storing the first, second and third type of data in a first, a second and a third database respectively, and receiving a query to search for one or more details corresponding to the user, wherein the one or more details are based on the unstructured continuous data of the user.

14 Claims, 11 Drawing Sheets

METHOD AND SYSTEM FOR GENERATING SEMANTIC RESPONSE TO QUERY

INCORPORATION BY REFERENCE

This application is based upon and claims the benefit of priority from Indian Patent Application number 202441026523, filed on Mar. 30, 2024, the disclosure of which is incorporated herein in its entirety by reference.

TECHNICAL FIELD

The present disclosure generally relates to data processing techniques and more particularly to an apparatus and a method for natural language processing of data and generating a semantic response to a query.

BACKGROUND ART

Medical experts spend an increasing amount of time with documentation of clinical findings of patients rather than spending their time examining the patients. Historically, medical information of the patients visiting the hospitals is maintained in physical form, i.e., in the form of papers and folders. Additionally, more than 80% of the prescriptions are handwritten. However, currently many healthcare institutions are digitizing patient health records by implementing some form of Electronic Medical Record (EMR) and Hospital Information Management System (HIMS) to operate the EMR. In addition to the time spent examining the patients, the medical experts spend additional hours entering the data into the hospital management system (HIMS) using an electronic device. A similar amount of time is spent when retrieving a response to a query.

For retrieving any medical related data of a patient from the EMR, the medical experts input a query in the EMR. The query is processed and a response to the query is fetched from a relevant database. The current systems for retrieving the response to the queries are not organized in that the information is simply displayed without any meaning. Further, it is problematic for the medical experts to manually browse through the data, as it can lead to wastage of time of the medical experts.

Hence, there is a need in the art to provide improved ways of retrieval of the response to the query made by the medical expert. Also, there is a need in the art to respond to the query in a meaningful way.

SUMMARY

The following presents a simplified summary of the subject matter in order to provide a basic understanding of some of the aspects of subject matter embodiments. This summary is not an extensive overview of the subject matter. It is not intended to identify key/critical elements of the embodiments or to delineate the scope of the subject matter. Its sole purpose to present some concepts of the subject matter in a simplified form as a prelude to the more detailed description that is presented later.

In one embodiment, the implementations of the present disclosure provide a method for generating a semantic response to a query. The method comprises receiving unstructured continuous data of a user, classifying the unstructured continuous data into a first type of data, by a first classification model, a second type of data, by a second classification model, and a third type of data, by a third classification model, wherein the second and third type of data includes name related data and event related data respectively. The method further comprises storing the first, second and third type of data in a first, a second and a third database respectively, receiving a query to search for one or more details corresponding to the user, wherein the one or more details are based on the unstructured continuous data of the user, retrieving, based on the received query, portions of at least the first type of data, the second type of data and the third type of data, from the first database, the second database, and the third database, respectively, and generating a semantic response based on the received query and the retrieved portions.

In another embodiment, the implementation of the present disclosure provides a system for generating a semantic response to a query. The system comprises a user device having an input/output unit configured to receive unstructured continuous data of a user, at least one memory, and at least one processor, a first database, a second database and a third database. The processor is coupled to the at least one memory and is configured to perform operations by classifying the unstructured continuous data into a first type of data, by a first classification model, a second type of data, by a second classification model, and a third type of data, by a third classification model, wherein the second and third type of data includes name related data and event related data respectively. The processor further performs the operations of storing the first, second and third type of data in the first, the second and the third database respectively, receiving a query to search for one or more details corresponding to the user, wherein the one or more details are based on the unstructured continuous data of the user, retrieving, based on the received query, portions of at least the first type of data, the second type of data and the third type of data, from the first database, the second database, and the third database, respectively, and generating a semantic response based on the received query and the retrieved portions.

The details of one or more examples are set forth in the accompanying drawings and the description below. Other features, objects, and advantages will be apparent from the description, drawings, and claims.

BRIEF DESCRIPTION OF DRAWINGS

The foregoing and further objects, features, and advantages of the present subject matter will become apparent from the following description of exemplary embodiments with reference to the accompanying drawings, wherein like numerals are used to represent like elements.

It is to be noted, however, that the appended drawings illustrate only typical embodiments of the present subject matter, and are, therefore, not to be considered for limiting of its scope, for the subject matter may admit to other equally effective embodiments.

Figure 1:
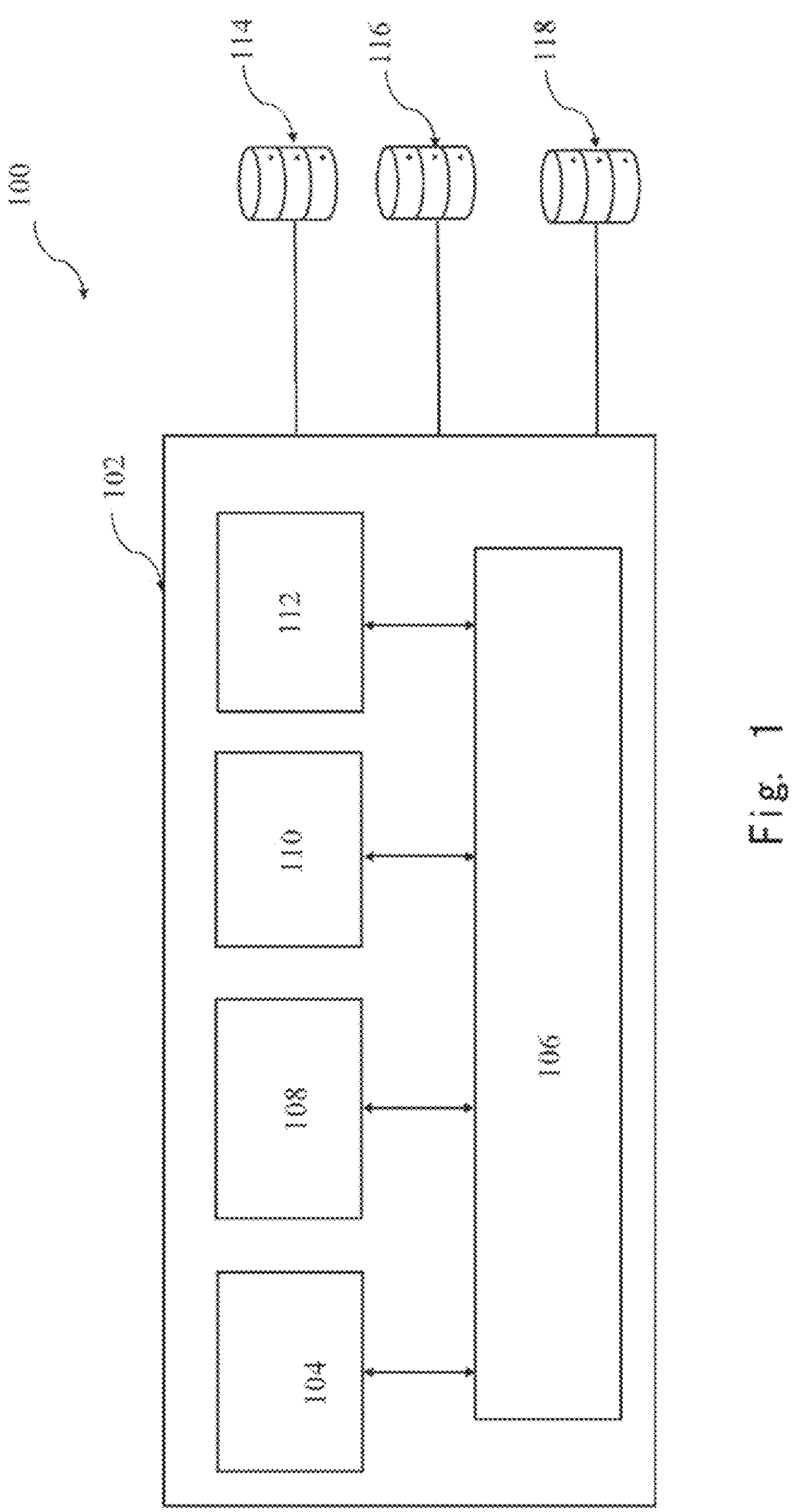

For a better understanding of the present disclosure, reference is made to the following description of an exemplary embodiment thereof, considered in conjunction with the accompanying drawings, in which:

FIG. 1 illustrates a simple block diagram of a system for generating a semantic response to a query, in accordance with an embodiment of the present subject matter.

Figure 2:
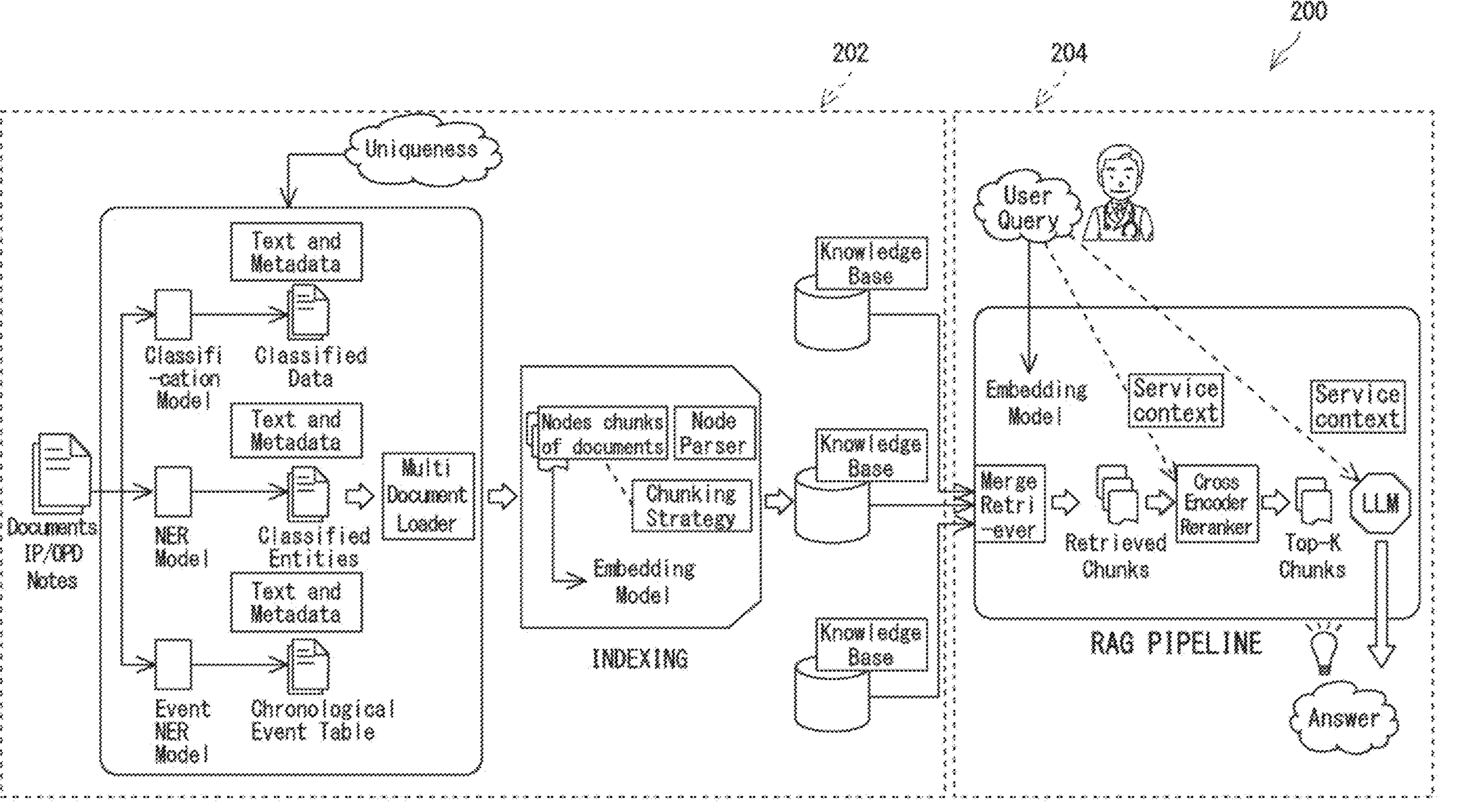

FIG. 2 illustrates a detailed block diagram of a system for generating a semantic response to a query, in accordance with an embodiment of the present subject matter.

Figure 3:
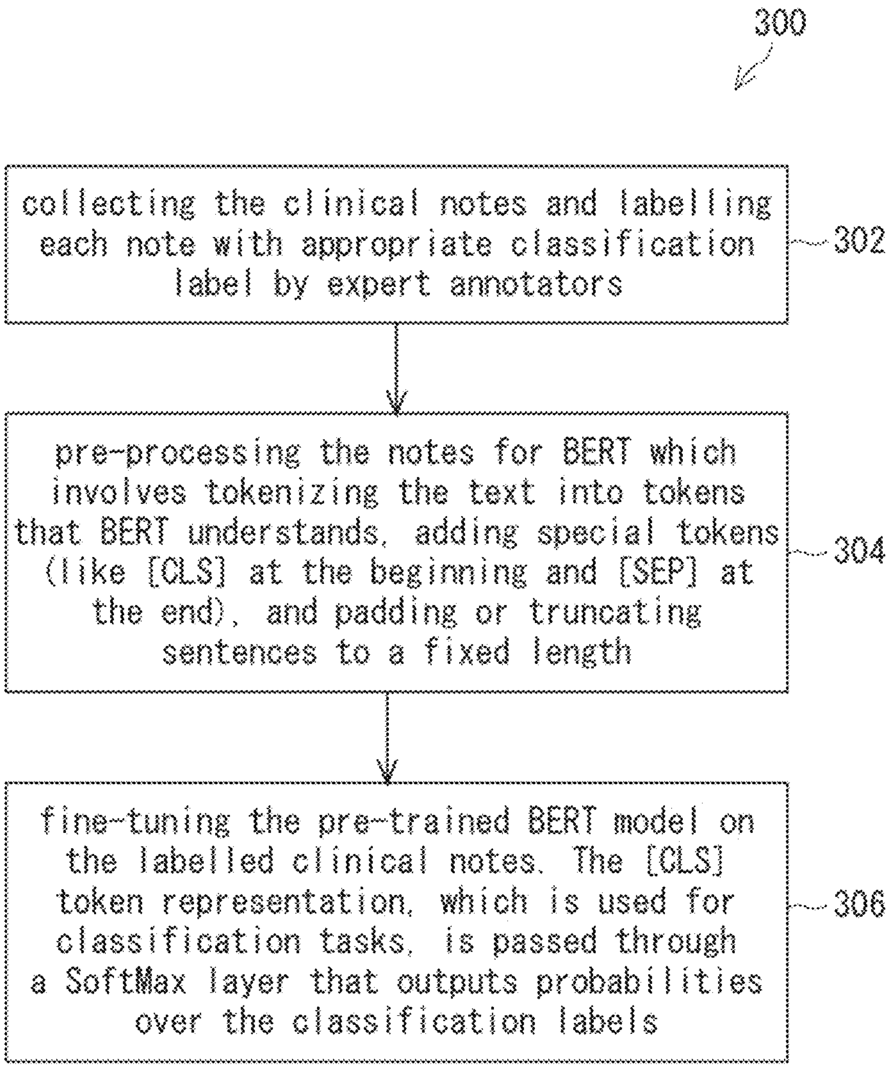

FIG. 3 illustrates a flowchart of a method for generating a first type of data by a first classification model, in accordance with an embodiment of the present subject matter.

Figure 4:
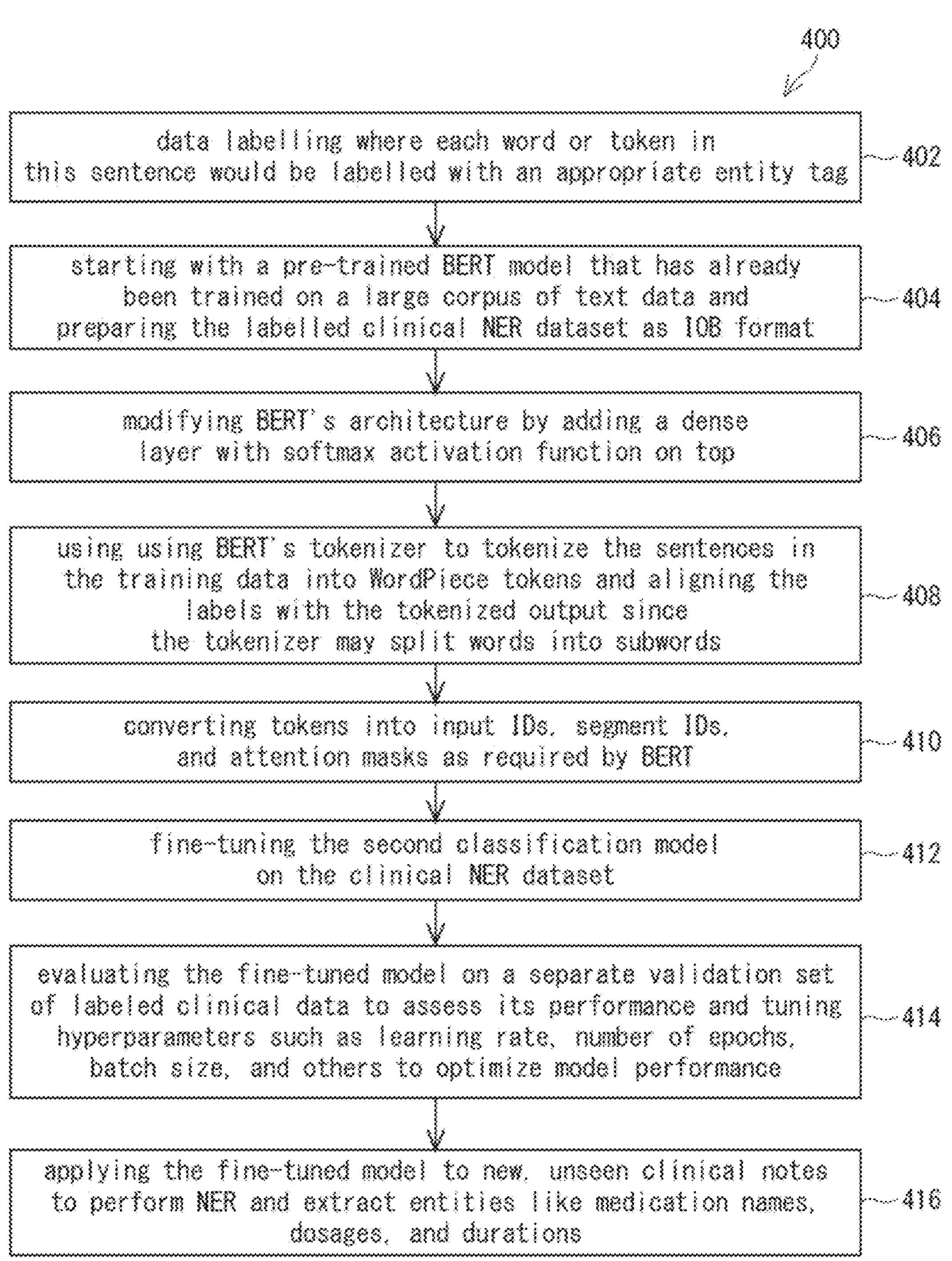

FIG. 4 illustrates a flowchart of a method for generating a second type of data by a second classification model, in accordance with an embodiment of the present subject matter.

Figure 5:
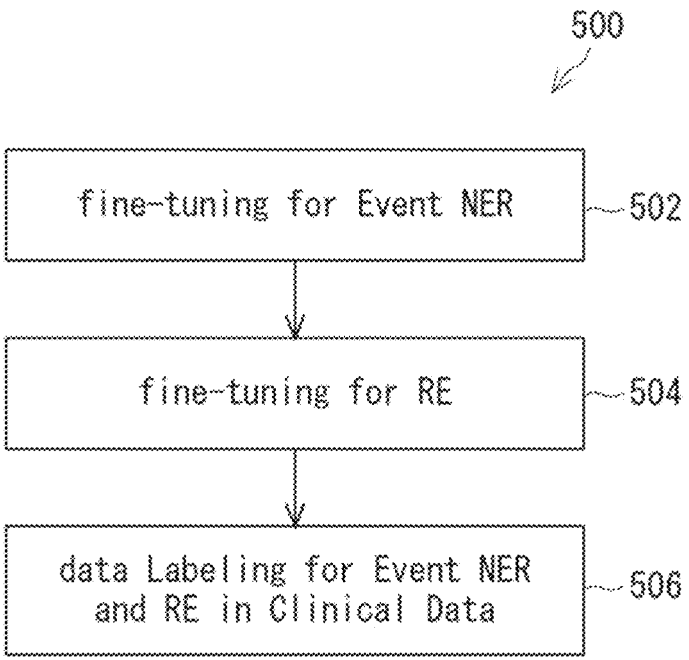

FIG. 5 illustrates a flowchart of a method for generating a third type of data by a third classification model in accordance with an embodiment of the present subject matter.

Figure 6:
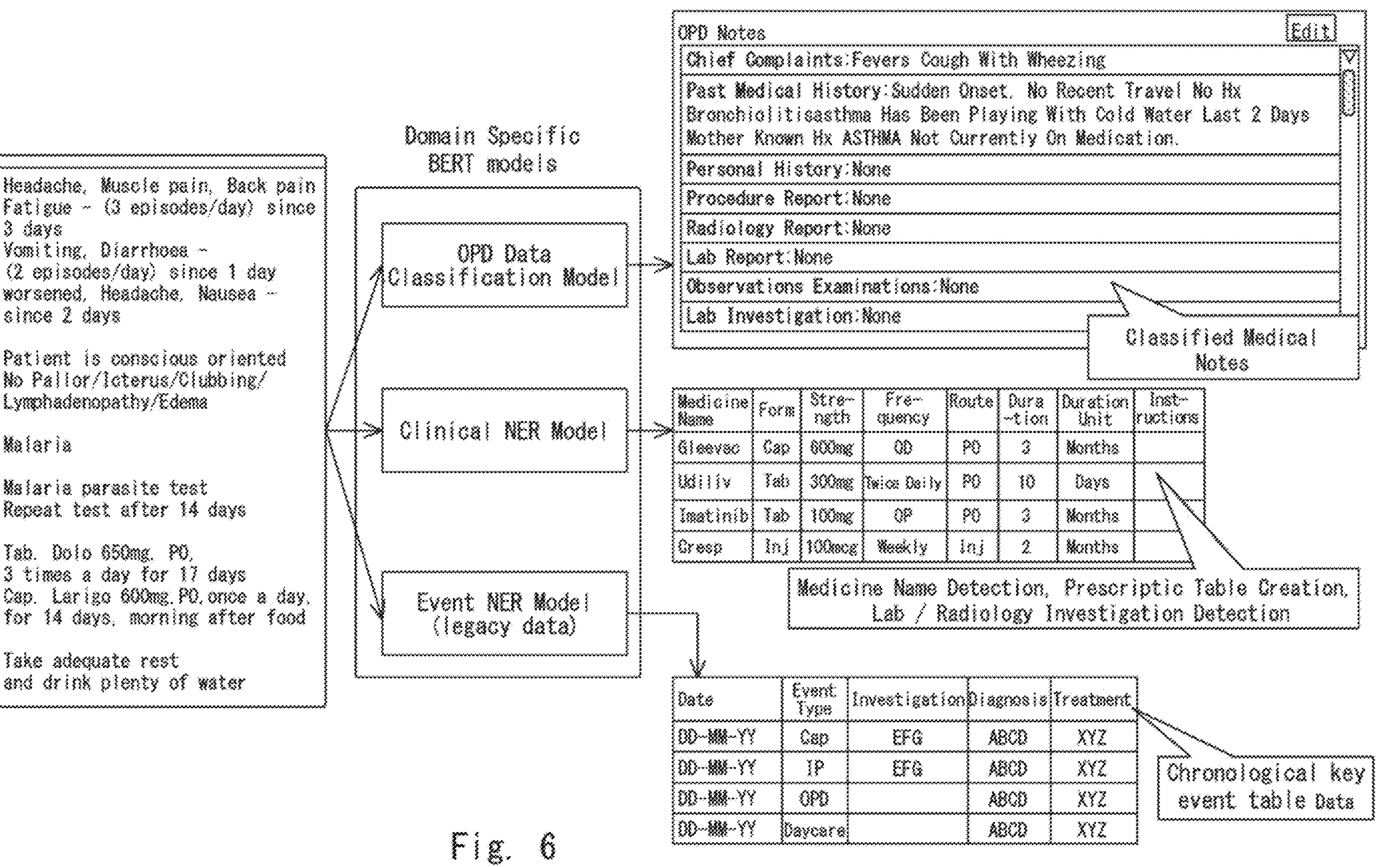

FIG. 6 illustrates an exemplary embodiment of classification of the unstructured continuous data into the first type of data, the second type of data and the third type of data, in accordance with one embodiment of the present disclosure.

Figure 7:
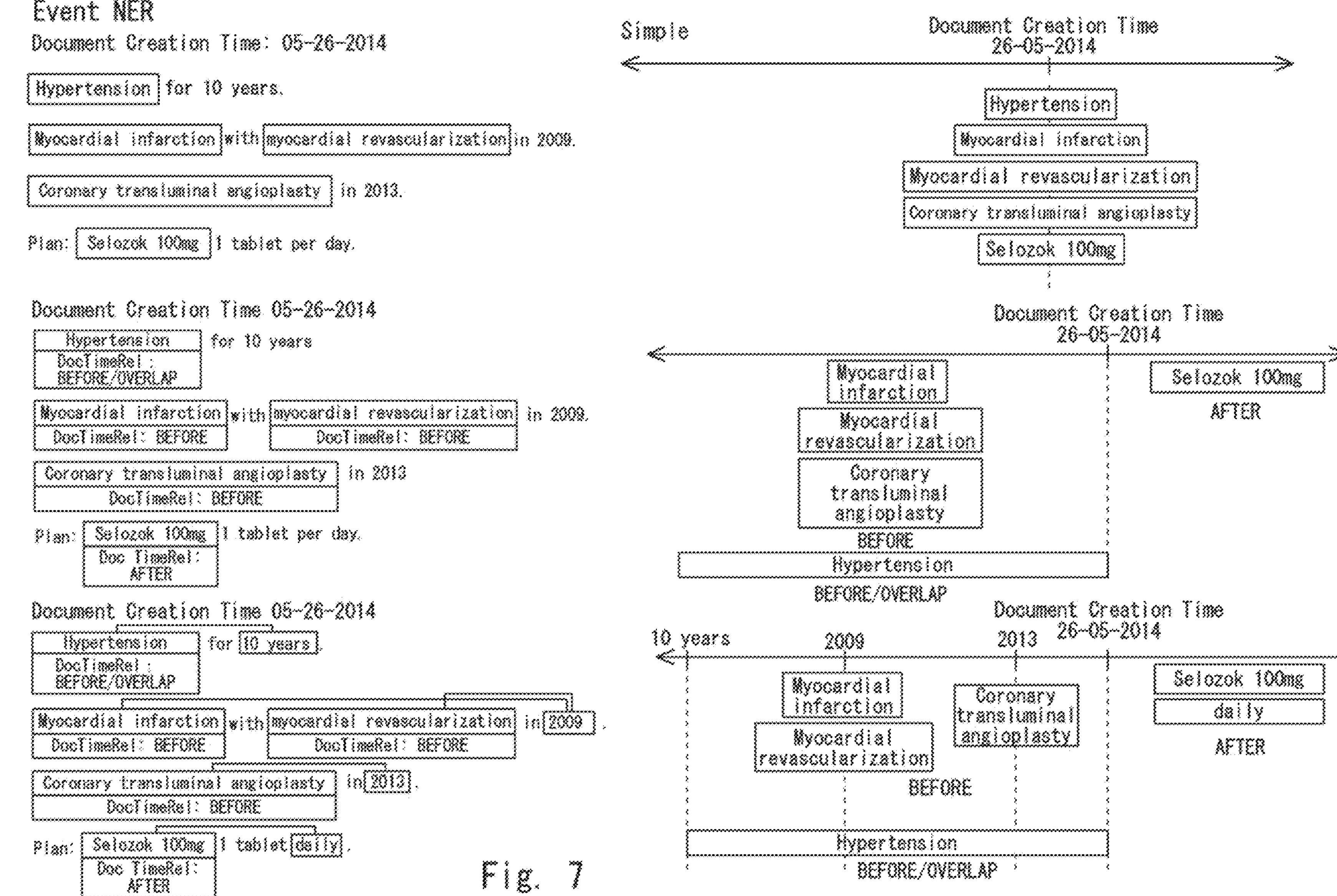

FIG. 7 illustrates an exemplary embodiment of classification of the unstructured continuous data into the third type of data in accordance with an embodiment of the present subject matter.

Figure 8A:
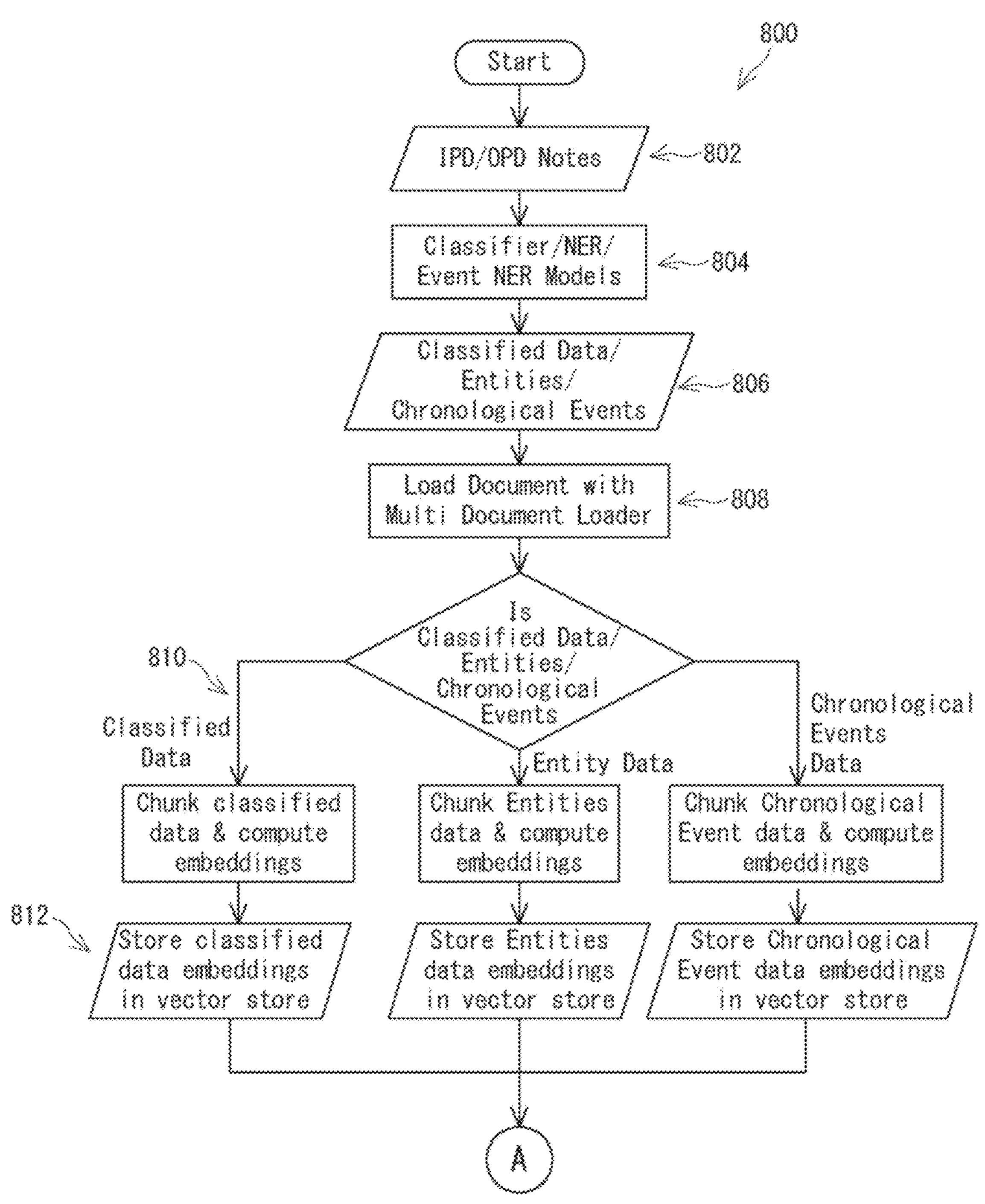
Figure 8B:
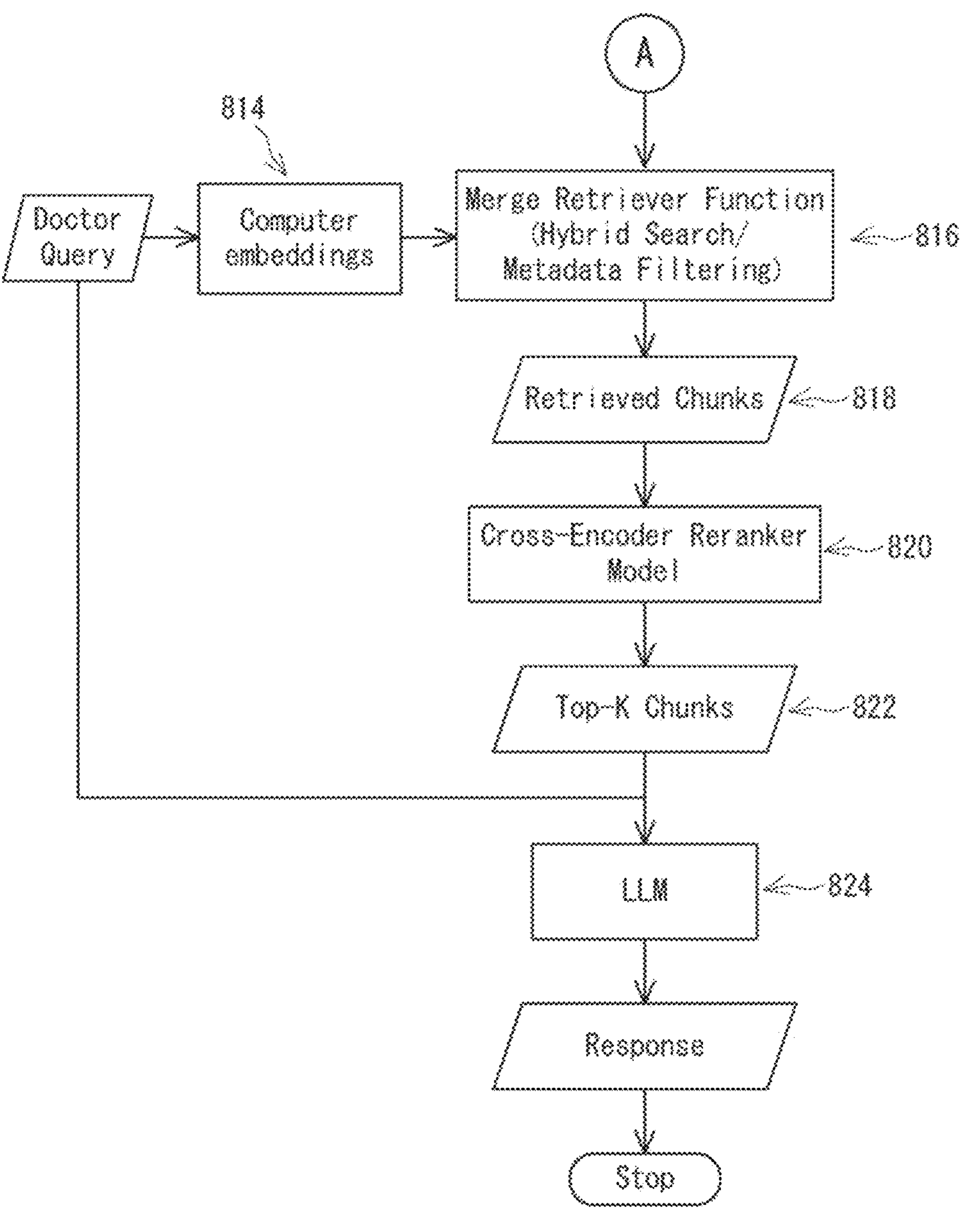

FIG. 8A illustrates a flowchart of a method for generating semantic response to a query in accordance with an embodiment of the present subject matter. FIG. 8B illustrates a flowchart of a method for generating semantic response to a query in accordance with an embodiment of the present subject matter.

Figure 9:
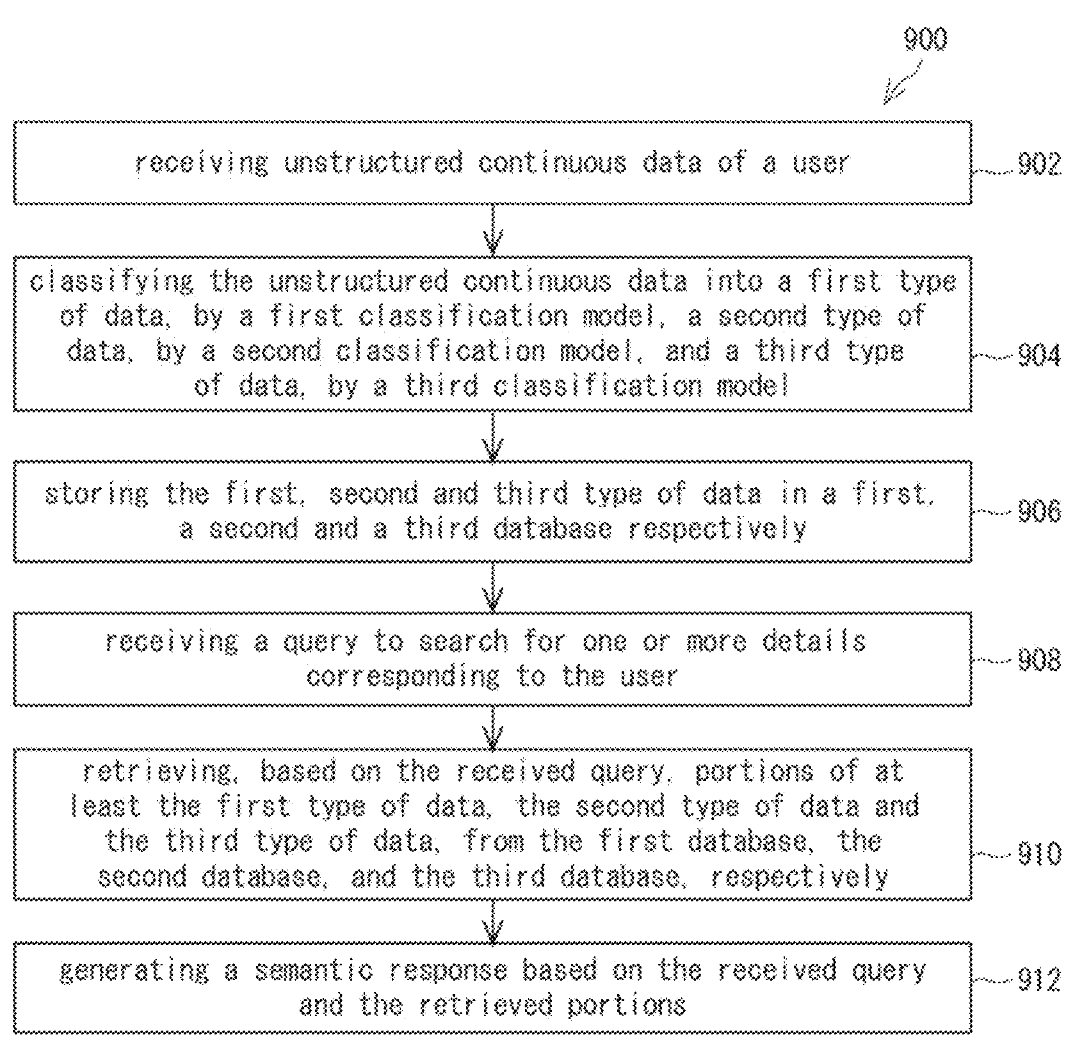

FIG. 9 illustrates a flowchart of a method for generating semantic response to a query in accordance with another embodiment of the present subject matter.

Figure 10:
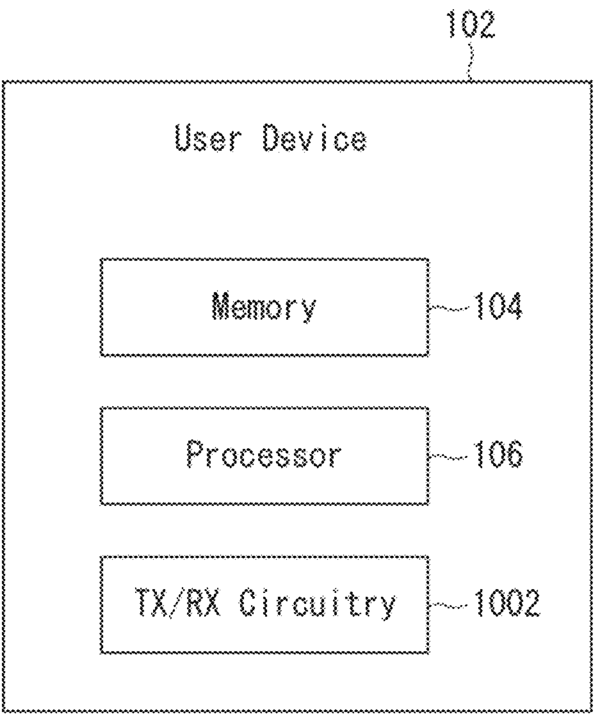

FIG. 10 illustrates a block diagram of a user device, in accordance with an embodiment of the present subject matter.

Although specific features of various embodiments may be shown in some drawings and not in others, this is for convenience only. Any feature of any drawing may be referenced and/or claimed in combination with any feature of any other drawing.

EXAMPLE EMBODIMENT

The embodiments of the present subject matter are described in detail with reference to the accompanying drawings. However, the present subject matter is not limited to these embodiments which are only provided to explain more clearly the present subject matter to the ordinarily skilled in the art of the present disclosure. In the accompanying drawings, like reference numerals are used to indicate like components.

This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Various aspects of the proposed system and method are described fully hereinafter with reference to the accompanying drawings. The same reference numbers in different drawings may identify the same or similar elements. The teachings disclosed may, however, be embodied in many different models with variations and should not be construed as limited to any specific structure or function presented throughout this disclosure. Rather, these aspects are provided so that this disclosure will be thorough and complete, and will fully convey the scope of the disclosure to those skilled in the art. It should be understood that any aspect disclosed herein may be embodied by one or more elements of a claim, and also that the following detailed description does not limit the claims.

Also, all logical units described and depicted in the FIGS. include the software and/or hardware components required for the unit to function. Further, each unit may comprise within itself one or more components which are implicitly understood. These components may be operatively coupled to each other and be configured to communicate with each other to perform the function of the said unit.

In an overview, the present disclosure relates to a medical setup where the medical practitioners face difficulty of entering and querying medical information related to various patients that visits the medical setup. As explained above, the medical practitioners face difficulty in retrieving a meaningful response to their queries. The present disclosure has been made keeping in mind the above mentioned difficulties. The present disclosure provides improved techniques for retrieving and presenting the retrieved information in a more meaningful form than in the conventional techniques.

FIG. 1 illustrates a basic block diagram of a system 100 in accordance with one embodiment of the present disclosure. The system 100 comprises a user device 102 having at least one memory 104 and at least one processor 106, an input/output unit 108, a display 110 and a transceiver 112. The system 100 further comprises a first database 114, a second database 116 and a third database 118.

The system 100 is configured to generate semantic response to a query provided by a medical expert. The system 100 receives unstructured continuous data of a user (e.g., a patient). The unstructured continuous medical information is input by medical practitioners (also referred to as "medical experts") in a medical setup. In one embodiment, the medical information may be received by the user device 102 which includes the input/output unit 108, such as a keyboard, microphone, etc. to receive the medical information. In one embodiment, the input/output unit 108 may include a stylus which may be used to enter the medical information on the display 110 present in the user device 102. In one embodiment, the stylus may be a digital pen, which can be used to write on a coded paper or on a digital pad, may not be directly located on the display. The medical practitioners use the input/output unit 108 to enter the medical information of a patient visiting the medical setup in a continuous manner. For example, when the patients visits the medical setup, the medical practitioners may ask the patient a plurality of questions, such as vital related questions, symptoms, medical history, allergies, chief complaints etc. Here entering the medical information in a continuous manner can be understood as entering the information on a single user interface on a single device. The unstructured form may be entered in free form with/without headings.

The received unstructured continuous data is stored in the at least one memory 104. The at least one processor 106 then classifies the received unstructured continuous data into a first type of data, a second type of data, and a third type of data. Each of the first type of data, the second type of data, and the third type of data, are classified using a first classification model, a second classification model, and a third classification model. The first, second, and third classification models are machine learning models, details of which are explained below. The classification of the unstructured continuous data is further explained in detail in conjunction with FIG. 2. The first type of data is the medical information related data. Some examples of the first type of data includes, but is not limited to, symptoms of the user as recorded by medical practitioner, chief complaints of the user, past medication history of the user, personal history of the user, radiology/Lab reports of the user, if available, etc.

The second type of data includes names related data. Some examples of the name related data includes, but is not limited to, name of the medicines prescribed to the user, name of the radiology/lab tests prescribed to the user, etc. Further, the third type of data includes event related data. Some examples of the event related data includes, but is not limited to, all the chronological events, such as date of visit of the user, date of radiology/lab tests done for the user, type of events, etc.

Each of the first type of data, second type of data, and third type of data, are stored in the first database 112, the second database 114, and the third database 116, respectively. The first database 112, the second database 114, and the third database 116, may be knowledge databases.

The medical practitioner may require a response to a query inputted in the system by the medical practitioner. The response may be desired by the medical practitioner to search for details corresponding to the user. The details are, for example, regarding the unstructured continuous data of the user. For example, the query may be to extract the information about the user, including symptoms of the user, name of the medicines prescribed to the user, and the date of visit (event) of the user.

In response to the query received from the medical practitioner, the at least one processor retrieves portions of at least the first type of data, the second type of data, and the third type of data, from the first, second and third database, respectively. For example, the medical practitioner may input a query to fetch details regarding a "user A". In response to the query, a response may be formulated which includes symptoms of the user (extracted from the first database), the name of the medicines prescribed to the user (extracted from the second database), and the date of visit of the user (extracted from the third database).

After retrieving the details from the first database, the second database and the third database, a semantic response to the query is generated. The semantic response includes a generation of the response to the query in a meaningful form understandable by the medical practitioner. For example, the at least one processor processes the information extracted from the first, the second and the third database display symptoms of the user, name of the medicine and the date of the visit by the user in a meaningful form (as explained later).

Referring to FIG. 2 now, a detailed block diagram of the system 100 for generating the semantic response to the query is disclosed, in accordance with one embodiment of the present disclosure. The system according to the FIG. 2 can be divided into 2 parts-a first part 202 where the unstructured continuous data is classified and stored in different databases, and a second part 204 where the medical practitioner sends the query and receives the semantic response to the query. The distinction between the two parts 202 and 204 is shown with a dotted line in FIG. 2.

The first part 202 begins with receiving the unstructured continuous data from the medical practitioner. The unstructured continuous data is medical data of a user, which is received when the user visits a medical setup to see the medical practitioner. Some examples of the unstructured continuous data includes symptoms of the user, chief complaints, laboratory/radiology tests, name of the medicines, date of visit of the user to the medical practitioner, etc.

Upon receiving the unstructured continuous data, the data is classified into the first type of data, the second type of data, and the third type of data using the first classification model, the second classification model and the third classification model, respectively. The first type of data includes user related data such as medical notes (e.g., chief complaints, post medical history, personal history, lab reports, if available, etc.). The second type of data includes name related data (e.g., medicine name, lab/radiology test names, etc.). The third type of data includes chronological event related data, such as date of visit of the user, date of OPD, etc.

The first classification model classifies the unstructured continuous data into clinical notes related to the user. In the context of clinical notes, the classification labels provided are used to structure and organize the notes into distinct sections that can help in various ways, such as tracking patient (i.e., the user) progress, facilitating billing, and ensuring comprehensive care. Each of these labels represent a specific type of information, for example:

1. Personal History: Information about the patient's medical, surgical, family, and social history.
2. Chief Complaints: The primary reasons for the patient's visit, usually symptoms or concerns.
3. Observations Examinations: Findings from physical examination and initial observations by a healthcare provider.
4. Diagnosis: The healthcare provider's medical determination, which is based on the history, chief complaints, and examinations.
5. Treatment Plan: The outline of the proposed treatments, which may include lifestyle changes, procedures, or follow-up visits.
6. Medicine Prescription: Specific medications prescribed, including dosage and instructions.

Example of OPD Notes with Text Classification Labels:

Doctor's Note: "Mr. X, a 52-year-old male with a history of hypertension and smoking, presents today complaining of intermittent chest pain for the past week. The pain is moderate in intensity, non-radiating, and associated with shortness of breath. No prior episodes like this. BP 145/90, heart rate regular at 78 bpm. Physical exam reveals no abnormalities. ECG shows no acute changes. Suspected angina. Prescribe sublingual nitroglycerin for chest pain as needed, aspirin 81 mg daily, and atorvastatin 20 mg at bedtime. Schedule a stress test and follow-up in one week. Advised patient to avoid strenuous activities and smoking."

Metadata:

Patient ID: 001234348
Age: 52 years
Gender: Male
Provider: Dr. Doctor, General Practitioner
Visit Date: Mar. 15, 2024
Note Type: Outpatient Visit Example of the First Type of Data by the First Classification Model:

Personal History: Hypertension, smoker
Chief Complaints: Intermittent chest pain, shortness of breath
Observations Examinations: BP 145/90, regular heart rate at 78 bpm, normal physical exam, unremarkable ECG
Diagnosis: Suspected Angina
Treatment Plan: Schedule stress test, avoid strenuous activities, smoking cessation advice
Medicine Prescription: Nitroglycerin (sublingual) as needed, Aspirin 81 mg daily, Atorvastatin 20 mg at bedtime To classify the unstructured continuous data into the first type of data, each section of the unstructured continuous data is first identified and extracted according to classification labels using text classification algorithms. The data is organized into the first database or electronic health record (EHR) system, with fields corresponding to each label (e.g., a field for Personal History, another for Chief Complaints, etc.). All of the classified and structured information are linked to the patient's unique identifier to ensure that it forms a part of their comprehensive medical record. Alongside this, metadata about the note (such as the date of the visit, the name of the clinician, and the department where the visit occurred) is also recorded. This adds context to the data and aids in chronological tracking and audit trails. This structured data can then be used for various purposes, such as analysing health trends, ensuring continuity of care, enhancing decision-making, and streamlining billing processes. This structured data will be used for summarization and quality analysis (QA) using the Retrieval-Augmented Generation (RAG) pipeline.

In one embodiment, the first classification model uses BERT (Bidirectional Encoder Representations from Transformers) and is a supervised learning model which requires labelled data for training. For text classification, the training data consists of text samples and their corresponding labels. Before being fine-tuned for specific tasks, BERT is pre-trained on a large corpus of text using two unsupervised tasks: Masked Language Modeling (MLM) and Next Sentence Prediction (NSP). This pre-training helps the model understand language patterns and contexts. BERT models are usually pre-trained on a large corpus of text, then fine-tuned for specific tasks like Sentence Pair Classification, Single Sentence Classification, Question Answering and Single Sentence Tagging.

After pre-training, BERT is fine-tuned on a labelled dataset for a specific task like classification. During fine-tuning, all the parameters of the model are updated with a small learning rate. The fine-tuned model learns to associate specific text patterns with the appropriate labels.

Referring to FIG. 3 now, a flowchart of a method 300 for generating a first type of data by a first classification model is illustrated. At step 302, the method comprises collecting the clinical notes and labelling each note with appropriate classification label by expert annotators. At step 304, the method comprises pre-processing the notes for BERT which involves tokenizing the text into tokens that BERT understands, adding special tokens (like [CLS] at the beginning and [SEP] at the end), and padding or truncating sentences to a fixed length. At step 306, the method comprises fine-tuning the pre-trained BERT model on the labelled clinical notes. The [CLS] token representation, which is used for classification tasks, is passed through a SoftMax layer that outputs probabilities over the classification labels. For example:

Input: "Patient complains of chest pain and shortness of breath after exercise."

Label: "Symptom"

During fine-tuning, the model learns that notes containing certain patterns (like "complains of chest pain") are associated with the label "Symptom."

At step 308, the method comprises passing many such labelled examples through the model for model training, using a loss function to calculate the error (difference between the predicted and actual labels), and updating the model weights via backpropagation to minimize this error. At step 310, the method comprises evaluating the fine-tuned model on a separate set of labelled clinical notes that it has never seen before to assess its classification accuracy. At step 312, the method comprises classifying new, unlabelled notes once fine-tuning is completed. When a new note comes in, the fine-tuned BERT model can predict the most likely label for that note.

Referring back to FIG. 2 now, the classification of the second type of data by the second classification model is now explained. Generating structured data from unstructured text, like doctors' notes, is a crucial step in extracting meaningful information that can be easily searched, analyzed, and acted upon. Named Entity Recognition (NER) plays a pivotal role in this process. NER is a form of natural language processing (NLP) that identifies and classifies key information (entities) in text into predefined categories.

In the context of doctors' notes, NER can help identify and categorize critical pieces of information such as patient symptoms, diagnoses, medications, dosages, lab results, and more. This structured extraction makes it easier to retrieve key pieces of information using a retrieval engine to generate correct responses for summarization and QA which will improve patient care, assist in research, and even automate certain aspects of healthcare management.

Incorporating metadata into structured Named Entity Recognition (NER) from clinical notes enhances the context and understanding of the extracted health information. Metadata can include details about the patient, healthcare provider, date of the note, and the clinical setting. Below are examples of structured NER applied to clinical notes, complete with relevant metadata to provide a comprehensive view.

Example 1: General Practitioner Visit

Metadata:
Patient ID: 001234567
Age: 42 years
Gender: Female
Provider: Dr. Doctor, General Practitioner
Visit Date: Mar. 15, 2024
Note Type: Outpatient Visit
Clinical Note:
"Patient presents with a sore throat and fatigue lasting two days. No fever. Advised to take acetaminophen and gargle with salt water."
Structured NER Output:
Symptoms: Sore throat, fatigue
Duration: Two days
Recommendations: Acetaminophen, salt water gargle Example 2: Psychiatry Consultation Metadata:
Patient ID: 004567890
Age: 35 years
Gender: Female
Provider: Dr. Doctor, Psychiatrist
Visit Date: Apr. 1, 2024
Note Type: Initial Consultation
Clinical Note:
"Consultation for long-standing anxiety and recent panic attacks. The patient reports difficulty sleeping. Starting on Zoloft 50 mg with plans to adjust based on response."
Name Related Output:
Symptoms: Anxiety, panic attacks, difficulty sleeping
Medication: Zoloft
Dosage: 50 mg daily The determination of the second type of data, i.e., the name related data, is one of the most pivotal data processing tasks in the field of NLP. It aims to locate and categorize key information, i.e., entities, in text data. These 'entities' can be any word or any sequence of words that consistently refer to the same thing. Once the unstructured continuous data is received, the second classification model detects the entities in text and categorizes the entities into named classes. Some of the most common entity classes in clinical notes are:

1. Medicine_Name: This is the name of the medication.
Example: "Patient has been prescribed Metformin . . . "
2. Medicine_Form: This describes the form in which the medicine to be administered.
Example: " . . . in the form of extended-release tablets . . . "
3. Medicine_Strength: This is the concentration or potency of the medicine.
Example: " . . . each tablet containing 500 mg . . . "
4. Medicine_Dose: This is the amount of medication to be taken at one time.
Example: " . . . the dose is one tablet . . . "
5. Medicine Route: This describes how the medicine is to be administered.
Example: " . . . to be taken orally . . . "
6. Medicine_Frequency: This indicates how often the medicine should be taken.
Example: " . . . twice daily . . . "
7. Medicine_Duration: For duration, the label Time_exp_Duration is used instead, indicating the length of time the medication should be taken.
Example: " . . . for a duration of 14 days . . . "
8. Medicine_Instruction: This provides specific directions related to the medication's use.
Example: " . . . with meals to reduce gastrointestinal upset . . . "

Entities into the context of a complete clinical note:

"Clinical Note: The patient has been diagnosed with Type 2 diabetes and is prescribed Metformin in the form of extended-release tablets, each containing 500 mg. The prescribed dose is one tablet taken orally twice daily with meals. The duration of this prescription is 14 days, and it's essential to monitor blood glucose levels throughout this period. Instructions also include taking the medication with meals to reduce the risk of gastrointestinal upset."

Each entity extracted from the above note along with metadata information provides critical information that contributes to a comprehensive understanding of the patient's medication regimen which will be further used and processed by the RAG pipeline for QA and summarization.

The second classification model uses BERT (Bidirectional Encoder Representations from Transformers) which are supervised learning models. The second classification model using BERT is trained on annotated datasets where entities within the text are labelled according to predefined categories (like Medicine_Name, Medicine_Dose, etc.). The model learns from these examples to predict the categories of entities in new, unseen text. BERT is designed to pre-train deep bidirectional representations by joint conditioning on both the left and right context in all layers. As a result, the pre-trained BERT model can be fine-tuned with just one additional output layer to create state-of-the-art models for a wide range of tasks, such as NER, without substantial task-specific architecture modifications.

BERT uses a technique called WordPiece tokenization, splitting the input text into tokens that can be found in its vocabulary. This includes splitting unknown words into known subwords, which allows BERT to handle a wide range of vocabulary with a fixed-size vocabulary list. The tokenised text is converted into embeddings. This includes token embeddings, segment embeddings (to distinguish between different sentences), and position embeddings (to provide positional context). BERT is pre-trained on two unsupervised tasks: Masked Language Model (MLM) and Next Sentence Prediction (NSP). MLM randomly masks some percentage of the input tokens and predicts the original vocabulary of the masked word based on its context. NSP predicts if a given pair of sentences are contiguous in the original text or not.

After pre-training, BERT can be fine-tuned on NER tasks. For NER, the final hidden vectors corresponding to each token are fed into a classification layer. The classification layer predicts the probability distribution over the NER label set for each token. A key feature of BERT is its ability to generate deeply contextual word embeddings. So, the same word will have different embeddings based on its contextual use. This is particularly beneficial for NER, as the context in which a word is used can completely change its meaning and entity type. During training, the model uses labelled data to adjust its weights using backpropagation, based on the errors it makes. For inference, it applies these weights to new, unseen data to predict the entities.

Referring to FIG. 4 now, a flowchart of a method 400 generating a second type of data by a second classification model is disclosed. At step 402, the method comprises data labelling where each word or token in this sentence would be labelled with an appropriate entity tag using the IOB (Inside, Outside, Beginning) tagging format. At step 404, the method comprises starting with a pre-trained BERT model that has already been trained on a large corpus of text data and preparing the labelled clinical NER dataset as IOB format. At step 406, the method comprises modifying BERT's architecture by adding a dense layer with softmax activation function on top. This layer will output the probability distribution over the NER label set for each token.

At step 408, the method comprises using BERT's tokenizer to tokenize the sentences in the training data into WordPiece tokens and aligning the labels with the tokenized output since the tokenizer may split words into subwords. At step 410, the method comprises converting tokens into input IDs, segment IDs, and attention masks as required by BERT. At step 412, the method comprises fine-tuning the second classification model on the clinical NER dataset. This involves feeding the tokenized input into BERT, which then outputs a vector representation for each token. The added dense layer takes these vectors and predicts the labels, comparing them against the actual labels in the dataset. An optimizer (like Adam) and loss function suitable for classification (like cross-entropy loss) may be used to update the weights in the entire network based on the error in prediction. This is iterated over the entire dataset multiple times (epochs) until the model performs well on the training data.

At step 414, the method comprises evaluating the fine-tuned model on a separate validation set of labeled clinical data to assess its performance and tuning hyperparameters such as learning rate, number of epochs, batch size, and others to optimize model performance. At step 416, the method comprises applying the fine-tuned model to new, unseen clinical notes to perform NER and extract entities like medication names, dosages, and durations.

Referring back to FIG. 2 now, the third classification model is now explained. For generating a chronological event table, the third classification model is deployed to identify and extract time-related entities from healthcare records. This process is refined through the use of datasets that have been specifically marked up with temporal information. The goal of extracting temporal relations is to sequence events and time-related data found within text. In the context of healthcare, 'events' refer to significant occurrences such as procedures, diagnoses, or tests, while 'temporal expressions' refer to specific times or durations mentioned in the text. These temporal expressions might be explicit times stated within the narrative or the time the document itself was created, known as the Document Creation Time (DCT).

There are two primary tasks in temporal relation extraction. The primary task includes identifying connections between an event and the DCT, where the DCT signifies the date when the document was created (Metadata). This can be performed by combining rule-based methods and leveraging existing Classification & NER tools. The second task includes identifying relationships among events and temporal expressions throughout the text, excluding the DCT. For this, models are trained on datasets with temporal annotations to recognize these temporal entities. Temporal relation extraction can be in two steps-identifying a relation between pairs of mentions (e.g., event and temporal expressions) and classifying this relation into a temporal relation type among a predefined set.

The third classification model in clinical notes, using BERT (Bidirectional Encoder Representations from Transformers) are supervised learning models. The first classification model can be subdivided into two models—the event NER model and the relation extraction (RE) mode. The Event NER component is responsible for identifying and categorizing important occurrences in text, such as medical procedures, diagnoses, or symptoms. Each event is labeled with a tag that categorizes it according to a predefined schema. Further, the RE component seeks to determine the relationships between identified events and time expressions. It classifies the nature of the relationship, such as before, after, during, or overlapping. Both Event NER and RE require annotated datasets where the entities and their relationships are manually labeled to train the model. This training involves learning to predict the correct label for unseen data.

Referring to FIG. 5 now, a flowchart of a method 500 for a method for generating a third type of data by a third classification model is disclosed. As explained above, the third classification model uses Bidirectional Encoder Representations from Transformer (BERT) techniques. BERT's bidirectional training is particularly useful for understanding the context surrounding each word, which is crucial for accurately identifying events and their temporal relationships. At step 502, the method comprises fine-tuning for Event NER. For event identification, the final hidden states corresponding to each input token can be used by an additional output layer that specializes in classifying whether a token is part of an event entity and which type of event it is (e.g., a procedure, diagnosis). At step 504, the method comprises fine-tuning for RE. After identifying the entities, BERT can be further fine-tuned to understand the relationships between entities. For RE, the input can consist of pairs of entities, and the model learns to predict the type of temporal relationship between them (e.g., before, after, concurrent with). At step 506, the method comprises data Labeling for Event NER and RE in Clinical Data. In a clinical setting, data labelling involves going through clinical notes and manually identifying:

Events: These could be anything from "administered medication" to "patient reports pain."

Temporal Expressions: Times or durations, such as "last night," "for three weeks," or "on April 20th."

Document Creation Time (DCT): The date when the note was created.

Relations: The annotators label the relationships between events and temporal expressions and between events and the DCT.

Further, the process of fine-tuning as mentioned above is explained now. A clinical note like "The patient was admitted to the ER on March 10th, complaining of acute chest pain" is annotated with:

Events: 'admitted to the ER', 'complaining of acute chest pain'

Temporal Expressions: 'on March 10th'

DCT: If the note was written on March 12th, this date is the DCT.

Relations: 'admitted to the ER' is related to 'on March 10th' by a temporal relation that could be labeled as "onDate."

The note is tokenized and inputted into BERT, which has been fine-tuned on similar annotated clinical data. BERT predicts not only the event entities but also the temporal relationships. For instance, BERT might predict that 'complaining of acute chest pain' happened "before" the DCT if the patient had been in pain for several days before writing the note. During training, BERT's model parameters are adjusted to minimize the prediction error on the labeled dataset. The model's predictions are compared against a validation set to assess its accuracy and ability to generalize.

The output from the third classification model will take the form of organized data accompanied by metadata, which will serve as input for the Retrieval-Augmented Generation (RAG) pipeline to enhance and refine summarization and question-answering capabilities.

Referring back to the FIG. 2 now, once the first type of data, the second type of data and the third type of data have been obtained, the indexing of the first type of data, the second type of data and the third type of data is performed. The indexing may be performed so as to store the first type of data, the second type of data and the third type of data into the first, second and third databases respectively. For example, with the help of indexing, the first type of data may be stored in the first database, the second type of data may be stored in the second database and the third type of data may be stored in the third database.

Before storing the first, second and third type of data in the first, second and third databases, the first, second and third type of data is split into chunks because of the vast amount of data. For each chunk, embeddings is computed by feeding them into an embedding model. The embedding model may use mathematical equations to make correlations between the first, second and third type of data and the relevant database (from the first, second and third databases). This correlation helps in retrieving the data when a response has to be obtained in response for a query.

When a query about a patient is received from a medical practitioner, the query is fed to the Retrieval-Augmented Generation (RAG) pipeline. In the RAG pipeline, the query is fed into the embedding model for retrieval of a response to the query. For example, the query may be divided into small segments to identify one or more keywords from the query. Same embeddings are computed on the keywords retrieved from the query. Based on the correlations present in the embedding model, the first, second and the third databases outputs the results which are then reranked using a cross-encoder reranker.

The cross-encoder reranker helps in improving the final results to the queries. The cross-encoder helps to filter the set of results retrieved from the first, the second and third databases. For example, there may be 100 results received from the first, second and the third databases in the initial search, which may then be filtered by the cross-encoder reranker to narrow down the queries.

Also in this RAG pipeline, hybrid search may be used, i.e., keyword based search followed by the semantic search. Keyword-based search helps improve the accuracy of the retrieval based on classified entities stored. Further, an ensemble retriever helps combine results both from keyword-based search as well as from the embedding-based retriever. In the ensemble retriever different weights are defined to the embedding based search as well as the keyword based search. This setup of the RAG pipeline makes it powerful to attain a superior degree of precision and specificity in responses, grounded in factual information The query is also fed to a language learning model (LLM). The LLM helps in generating semantic response from the keywords retrieved from the first, second, and third databases. Thus, based on the first type of data, the second type of data, and the third type of data retrieved from the first, second, and third databases, along with the output from the LLM, a response, to the query received from the medical practitioner, is generated.

Referring to FIG. 6 now, an exemplary embodiment of the classification of the unstructured continuous data into the first type of data, the second type of data and the third type of data is shown. The left side of the figure shows the unstructured continuous data which has been obtained by a medical practitioner from a user. This unstructured continuous data specifies the details of the user. For example, the unstructured continuous data may include chief complaints of the user, details of the laboratory tests prescribed to the user, name of the medicines and other recommendations by the medical practitioners for the user.

This unstructured continuous data is classified into the first type of data, the second type of data and the third type of data by the first classification model, the second classification model and the third classification model. The first classification model may include Out Patient Department (OPD) data classification model. The first classification model classifies the unstructured continuous data in the first type of data. As shown on the right, the first type of data is the medical notes related data including, but not limited to the fields such as chief complaints, past medical history, personal history, procedure report, radiology report, lab report, observations examinations, lab investigation, etc.

Similarly, the unstructured continuous data is classified by the second classification model into the second type of data. The second type of data, as shown on the right hand side, includes medicine name, form of medicine, strength of the medicine, frequency of the medicine, route of the medicine, duration and duration unit for which the medicine has been prescribed, and/or any other instructions as prescribed by the medical practitioner. The steps performed by the second classification model has been explained above.

Further, the unstructured continuous data is classified by the third classification model into the third type of data. The third classification model includes, event named entity recognition (NER) model. One example of the third type of data includes, but not limited to, chronological key event table data such as date, event type, type of investigation, type of diagnosis and treatment prescribed to the user.

Referring to FIG. 7 now, another example embodiment of the classification of the unstructured continuous data into the third type of data and the representation of the third type of data is shown, in accordance with one embodiment of the present disclosure. As shown, the unstructured continuous data is classified into the third type of data by the third classification model (as explained above). Also, as mentioned above, the third type of data is the event related data identified from the unstructured continuous data.

For example, event date is May 26, 2014, notes related to the chief complaints of the user (e.g., hypertension, myocardial infarction, coronary transluminal angioplasty) were made by the medical practitioner along with the events related to each chief complaint. Further, medicine along with the frequency of intake of the medicine as prescribed to the user is also noted. The third type of data, i.e., the event data mentioned in the unstructured continuous data is represented in a graphical form clearly highlighting the chronological events.

Referring to FIG. 8A and FIG. 8B now, a flowchart of a method for generating semantic response to a query is disclosed in accordance with one embodiment of the present disclosure. At step 802, the method comprises receiving the IPD/OPD notes about a user from a medical practitioner. The IPD/OPD notes are in the form of unstructured continuous data. At step 804, the method comprises classifying the received notes by the first classification model (classifier), the second classification model (Named entity recognition (NER) model), the third classification model (Event named entity recognition (NER) model). At step 806, the method comprises classifying the received notes as the first type of data (classified data), the second type of data (entities), and the third type of data (chronological events) by the first classification model, the second classification model and the third classification model.

At step 808, the method comprises providing the first type of data, the second type of data and the third type of data to a multi document loader which helps to process the multiple documents. At step 810, the method comprises feeding each of the first type of data, the second type of data and the third type of data to a RAG pipeline for generating chunk classified data and computing the embeddings using embedding model. This process of generating the chunks and computing embeddings is performed for each of the first type of data, the second type of data and the third type of data.

At step 812, the method comprises storing the data obtained after generating the chunk and computing embeddings in the first database (vector store), the second database (vector store) and the third database (vector store). The storage of the data in different databases ensures a faster and superior degree of precision and specificity in responses.

Next set of processes 814-824 are performed when a query is received from a medical practitioner (for example, a doctor). At step 814, the method comprises computing embeddings on the query received from the medical practitioner. At step 816, the method comprises merging the retriever functions to perform hybrid search/metadata filtering. At step 818, the method comprises retrieving the chunks from the first, second and the third databases. At step 820, the method comprises providing a cross-encoder re-ranker model which helps to identify Top-k chunks. At step 822, the method comprises feeding the query from the medical practitioner along with the Top-K chunks to a language learning model. At step 824, the method comprises generating a response based on output from the language learning model.

Referring to FIG. 9 now, a flowchart of a method for generating a semantic response to a query is disclosed, in accordance with one embodiment of the present disclosure. At step 902, the method comprises receiving unstructured continuous data of a user. At step 904, the method comprises classifying the unstructured continuous data into a first type of data, by a first classification model, a second type of data, by a second classification model, and a third type of data, by a third classification model, wherein the second and third type of data includes name related data and event related data respectively. At step 906, the method comprises storing the first, second and third type of data in a first, a second and a third database respectively.

At step 908, the method comprises receiving a query to search for one or more details corresponding to the user, wherein the one or more details are based on the unstructured continuous data of the user. At step 910, the method comprises retrieving, based on the received query, portions of at least the first type of data, the second type of data and the third type of data, from the first database, the second database, and the third database, respectively. At step 912, the method comprises generating a semantic response based on the received query and the retrieved portions.

Referring to FIG. 10 now, FIG. 10 illustrates a block diagram of the user device 102 in accordance with an embodiment of the present subject matter. The device 102 may be any computing device present with the medical practitioner for receiving the information related to the user. The various modules in the user device 102 can be embodied as a hardware that includes, without limitation, the at least one memory 104, the at least one processor 106, transmitter/receiver circuitry 1002, and programmable logic or software.

The at least one memory 104, which may include both read-only memory (ROM) and random access memory (RAM), can provide instructions and data to the at least one processor 106. The at least one memory 104 and the at least one processor 106 may be operatively coupled. The at least one memory 104 may store computer readable instructions/computer program code. The at least one processor 106 in the device 102 may train the first, second and the third classification models.

In the context of this document, the "memory" (also referred to as "computer-readable media" or "computer-readable medium") may be any non-transitory media or medium or means that can contain, store, communicate, propagate or transport the instructions for use by or in connection with an instruction execution system, apparatus, or device, such as a computer. The term "non-transitory," as used herein, is a limitation of the medium itself (i.e., tangible, not a signal) as opposed to a limitation on data storage persistency (e.g., RAM vs. ROM).

The transmitter/receiver (TX/RX) circuitry 1002 may comprise a transmitter and a receiver that can enable the device 102 to transmit data to or receive data (e.g., the input image of the crop) from the network or plurality of databases.

The at least one processor 106 can be a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor may also be implemented as a combination of computing devices, e.g., a combination of a DSP and a microprocessor, a plurality of microprocessors, one or more microprocessors in conjunction with a DSP core, or any other such configuration. The processor can include the logic circuitry with hardware, firmware, and software architecture frameworks for facilitating image processing.

The steps of a method (e.g., method 800, 900) described in connection with the embodiments disclosed herein may be embodied directly in hardware (e.g., device 102), in a software module executed by the at least one processor 106, or in a combination of the two. If implemented in software, the functions may be stored on or transmitted over as one or more instructions or code on a tangible, non-transitory computer-readable medium (e.g., the at least one memory 104). A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD ROM, or any other form of storage medium known in the art. A storage medium is coupled to the processor such that the processor can read information from, and write information to, the storage medium.

In the several embodiments provided in this application, the disclosed system, device, and method may be implemented in another manner. For example, some features of the method embodiments described above may be ignored or not performed. The described device embodiments are merely examples.

The term based on is not exclusive and allows for being based on additional factors not described unless the context clearly dictates otherwise. In addition, throughout the specification, the meaning of "a", "an" and "the" include plural references. The meaning of "in" includes "in" and "on"

As used herein the terms "and" and "or" may be used interchangeably to refer to a set of items in both the conjunctive and disjunctive in order to encompass the full description of combinations and alternatives of the items. In either case, the set is to be interpreted as meaning each of the items singularly as alternatives, as well as any combination of the listed items.

The description above merely illustrating the technical spirit of the present disclosure, and various changes and modifications may be made by those skilled in the art without departing from the essential characteristics of the present disclosure. Therefore, the embodiments of the present disclosure described above may be implemented separately or in combination with each other.

The embodiments disclosed in the present disclosure are intended to illustrate rather than limit the scope of the present disclosure, and the scope of the technical spirit of the present disclosure is not limited by these embodiments. The scope of the present disclosure should be construed by claims below, and all technical spirits within a range equivalent to claims should be construed as being included in the right scope of the present disclosure.

While only certain features have been illustrated and described herein, many modifications and changes will occur to those skilled in the art. It is, therefore, to be understood that the appended claims are intended to cover all such modifications and changes as fall within the true spirit of the disclosure.

For example, the whole or part of the example embodiments disclosed above can be described as, but not limited to, the following supplementary notes.

(Supplementary Note 1)

A method for generating a semantic response to a query, the method comprising:

receiving unstructured continuous data of a user;

classifying the unstructured continuous data into:

a first type of data, by a first classification model, a second type of data, by a second classification model, and a third type of data, by a third classification model, wherein the second and third type of data includes name related data and event related data respectively;

storing the first, second and third type of data in a first, a second and a third database respectively;

receiving the query to search for one or more details corresponding to the user, wherein the one or more details are based on the unstructured continuous data of the user;

retrieving, based on the received query, portions of at least the first type of data, the second type of data and the third type of data, from the first database, the second database, and the third database, respectively; and generating the semantic response based on the received query and the retrieved portions.

(Supplementary Note 2)

The method according to Supplementary note 1, wherein the unstructured continuous data comprises medical related data.

(Supplementary Note 3)

The method according to Supplementary note 1, wherein the first type of data includes medical related data of the user.

(Supplementary Note 4)

The method according to Supplementary note 1, wherein the name related data includes names of medicines and tests prescribed to the user.

(Supplementary Note 5)

The method according to Supplementary note 1, wherein the event related data includes chronological events related to the user.

(Supplementary Note 6)

The method according to Supplementary note 1, wherein the first, second and third classification models comprises machine learning models, and are optimized using an optimizer.

(Supplementary Note 7)

The method according to Supplementary note 1, wherein retrieving the portions is performed by Retrieval Augmented Generation (RAG) techniques.

(Supplementary Note 8)

A system for generating a semantic response to a query, the system comprising:

a user device having:

an input/output unit configured to receive unstructured continuous data of a user, at least one memory, and at least one processor;

a first database;

a second database;

a third database;

wherein the processor is coupled to the at least one memory and is configured to perform operations by:

classifying the unstructured continuous data into:

a first type of data, by a first classification model, a second type of data, by a second classification model, and a third type of data, by a third classification model, wherein the second and third type of data includes name related data and event related data respectively;

storing the first, second and third type of data in the first, the second and the third database respectively;

receiving a query to search for one or more details corresponding to the user, wherein the one or more details are based on the unstructured continuous data of the user;

retrieving, based on the received query, portions of at least the first type of data, the second type of data and the third type of data, from the first database, the second database, and the third database, respectively; and generating a semantic response based on the received query and the retrieved portions.

(Supplementary Note 9)

The system according to Supplementary note 8, wherein the unstructured continuous data comprises medical related data.

(Supplementary Note 10)

The system according to Supplementary note 8, wherein the first type of data includes medical related data of the user.

(Supplementary Note 11)

The system according to Supplementary note 8, wherein the name related data includes names of medicines and tests prescribed to the user.

(Supplementary Note 12)

The system according to Supplementary note 8, wherein the event related data includes chronological events related to the user.

(Supplementary Note 13)

The system according to Supplementary note 8, wherein the first, second and third classification models comprises machine learning models, and are optimized using an optimizer.

(Supplementary Note 14)

The system according to Supplementary note 8, wherein retrieving the portions is performed by Retrieval Augmented Generation (RAG) techniques.

What is claimed is:

1. A method for generating a semantic response to a query, the method comprising:

receiving unstructured continuous data of a user;

classifying the unstructured continuous data into:

a first type of data, by a first classification model, a second type of data, by a second classification model, and a third type of data, by a third classification model, wherein the second and third type of data includes name related data and event related data respectively;

storing the first, second and third type of data in a first, a second and a third database respectively;

storing the first type of data in the first database, the second type of data in the second database, and the third type of data in the third database, respectively;

organizing the first type of data in the first database with fields corresponding to classification labels;

linking the first type of data, the second type of data, and the third type of data to a unique identifier of the user;

recording metadata about the unstructured continuous data, the metadata including a date of visit, a name of a clinician, and a department where the visit occurred;

using the first type of data, the second type of data, the third type of data, and the metadata in a Retrieval-Augmented Generation (RAG) pipeline for summarization and quality analysis;

receiving the query to search for one or more details corresponding to the user, wherein the one or more details are based on the unstructured continuous data of the user;

retrieving, based on the received query, portions of at least the first type of data, the second type of data and the third type of data, from the first database, the second database, and the third database, respectively; and generating the semantic response based on the received query, and the retrieved portions, and the metadata, wherein the semantic response includes information extracted from the first database, the second database, and the third database in a form understandable by a medical practitioner.

2. The method as claimed in claim 1, wherein the unstructured continuous data comprises medical related data.

3. The method as claimed in claim 1, wherein the first type of data includes medical related data of the user, the medical related data including one or more of symptoms of the user, chief complaints of the user, past medication history of the user, personal history of the user, and radiology or laboratory reports of the user.

4. The method as claimed in claim 1, wherein the name related data includes names of medicines and tests prescribed to the user.

5. The method as claimed in claim 1, wherein the event related data includes chronological events related to the user, and the chronological events are identified based on a connection between an event and a document creation time represented by the metadata.

6. The method as claimed in claim 1, wherein the first, second and third classification models comprises machine learning models, and are optimized using an optimizer, wherein the first classification model uses Bidirectional Encoder Representations from Transformers (BERT) fine-tuned on labelled clinical notes.

7. The method as claimed in claim 1, wherein retrieving the portions is performed by Retrieval Augmented Generation (RAG) techniques, wherein the first type of data, the second type of data, the third type of data, and the metadata are used in the Retrieval-Augmented Generation (RAG) pipeline for summarization and quality analysis.

8. A system for generating a semantic response to a query, the system comprising:

a user device having:

an input/output unit configured to receive unstructured continuous data of a user, at least one memory, and at least one processor, a first database;

a second database;

a third database;

wherein the processor is coupled to the at least one memory and is configured to perform operations by:

classifying the unstructured continuous data into:

a first type of data, by a first classification model, a second type of data, by a second classification model, and a third type of data, by a third classification model, wherein the second and third type of data includes name related data and event related data respectively;

storing the first, second and third type of data in the first, the second and the third database respectively;

storing the first type of data in the first database, the second type of data in the second database, and the third type of data in the third database, respectively;

organizing the first type of data in the first database with fields corresponding to classification labels;

linking the first type of data, the second type of data, and the third type of data to a unique identifier of the user;

recording metadata about the unstructured continuous data, the metadata including a date of visit, a name of a clinician, and a department where the visit occurred;

using the first type of data, the second type of data, the third type of data, and the metadata in a Retrieval-Augmented Generation (RAG) pipeline for summarization and quality analysis;

receiving the query to search for one or more details corresponding to the user, wherein the one or more details are based on the unstructured continuous data of the user;

retrieving, based on the received query, portions of at least the first type of data, the second type of data and the third type of data, from the first database, the second database, and the third database, respectively; and generating the semantic response based on the received query, and the retrieved portions, and the metadata, wherein the semantic response includes information extracted from the first database, the second database, and the third database in a form understandable by a medical practitioner.

9. The system as claimed in claim 8, wherein the unstructured continuous data comprises medical related data.

10. The system as claimed in claim 8, wherein the first type of data includes medical related data of the user, the medical related data including one or more of symptoms of the user, chief complaints of the user, past medication history of the user, personal history of the user, and radiology or laboratory reports of the user.

11. The system as claimed in claim 8, wherein the name related data includes names of medicines and tests prescribed to the user.

12. The system as claimed in claim 8, wherein the event related data includes chronological events related to the user, and the chronological events are identified based on a connection between an event and a document creation time represented by the metadata.

13. The system as claimed in claim 8, wherein the first, second and third classification models comprises machine learning models, and are optimized using an optimizer, wherein the first classification model uses Bidirectional Encoder Representations from Transformers (BERT) fine-tuned on labelled clinical notes.

14. The system as claimed in claim 8, wherein retrieving the portions is performed by Retrieval Augmented Generation (RAG) techniques, the first type of data, the second type of data, the third type of data, and the metadata are used in the Retrieval-Augmented Generation (RAG) pipeline for summarization and quality analysis.

* * * * *